Nov. 27, 1956 R. V. LINDQUIST Plant Pat. 1,531
ROSE PLANT
Filed Jan. 5, 1956
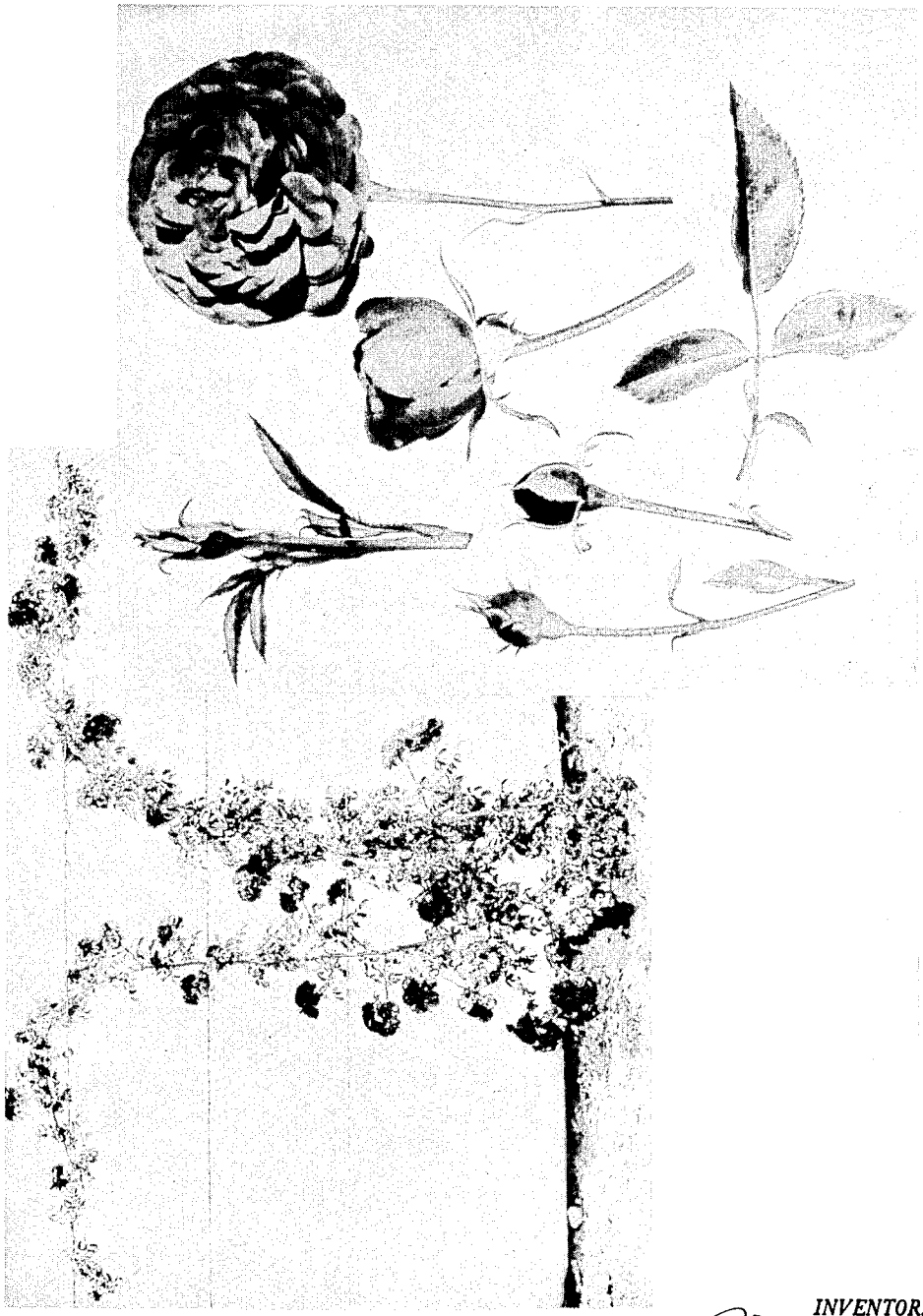
INVENTOR.
BY R. V. Lindquist
Robb & Robb
Attorneys United States Patent Office Plant Pat. 1,531
Patented Nov. 27, 1956

1,531

ROSE PLANT

Robert V. Lindquist, Hemet, Calif., assignor to Hemet Wholesale, Hemet, Calif., a partnership Application January 5, 1956, Serial No. 557,618

1 Claim. (Cl. 47—61)

The present invention relates to a new and distinct variety of rose plant which originated as a sport of the variety "Eutin" (unpatented), and is distinguished from the latter by its climbing habit of growth. The new variety was discovered by me in a cultivated block of "Eutin" roses which were being grown under my direction and supervision at Hemet, California.

At the time of my discovery, my attention was attracted to the new variety by the unusually vigorous and climbing habit of a particular plant of the "Eutin" block noted above. Upon closer examination thereof, I found that the parent variety had sported, and I thereupon promptly took steps to preserve, asexually reproduce and observe the sport for the purpose of determining whether its climbing habit was fixed and was transmissible by asexual reproduction. The climbing habit was fully confirmed by such observations and by asexual reproduction by budding, as performed by me at Hemet, California, and I have established that the climbing habit of growth of the new variety comes true to form and is transmissible through succeeding propagations.

In addition to being generally similar to the parent variety "Eutin," except that the latter is a bush rose and so far as I am aware has never exhibited any tendency toward a climbing habit, my new variety further differs in a few minor respects from the parent variety in that the flowers of the new variety are produced in smaller clusters and are borne on shorter stems than those of "Eutin."

In view of the general similarities, except as noted in the foregoing, it is unnecessary to describe or illustrate the new variety in detail herein, but for convenience, the accompanying drawing illustrates in black-and-white a typical specimen plant of the new variety, as well as typical specimens of the vegetative growth and flowers thereof in different stages of development and on a somewhat enlarged scale.

The following is a brief description of the new variety, with color terminology in accordance with Robert F. Wilson's Horticultural Colour Chart (hereinafter abbreviated as "Wilson") and Robert Ridgeway's Color Standards and Nomenclature (hereinafter abbreviated as "Ridgeway"), as indicated:

Type: Climber; outdoor; sport; for cut flowers and for garden decoration.
Class: Climbing hybrid polyantha.
Parentage: Sport of "Eutin."
Propagation: Holds its distinguishing characteristics through succeeding propagations by budding.

FLOWER

Locality where grown and observed: Hemet, California.
Flowers borne: Several to stem; in irregular, rounded clusters; on strong stems of from medium length to long.
Quantity of bloom: Free, outdoors.
Continuity: Intermittent during growing season.
Fragrance: None.

Bud:

*Peduncle.*—Short; slender; bending; usually rough; with numerous gland-tipped cilia and few hairs.

*Before calyx breaks.*—Size—small. Form—short; ovoid; with foliaceous appendages and few gland-tipped cilia; usually with slender, bristle-like foliaceous parts extending beyond the tip of the bud equal to ¼ or more of its length.

*As calyx breaks.*—Color—near Tyrian Purple, Plate 727, page 159 (Wilson).

*Sepals.*—Inner surface—with fine, woolly tomentum. Margins—with few foliaceous appendages and gland-tipped cilia.

*As first petal opens.*—Size—small. Form—ovoid. Color: Outside—near Rose Red, Plate 724/2, page 158 (Wilson); inside—near Rose Red, Plate 724, page 158 (Wilson).

*Opening.*—Opens up well; is not retarded from opening by cold, hot, wet or dry weather.

Bloom:

*Size (when fully open).*—Average size of climbing hybrid polyantha; from 1½ inches to 2 inches in diameter.

*Petalage.*—Double; from 20 to 30 petals, plus 5 to 10 petaloids; arranged regularly.

*Form.*—Cupped at first, but becoming open-cupped; petals being at first somewhat loosely cupped, with tips rolled outward, and remaining somewhat loosely cupped, with tips rolled outward, later at maturity.

Petals:

*Texture.*—Medium thin; soft. Inside—velvety. Outside—satiny.

*Shape.*—Outside—oval. Intermediate—oval. Inside—oval.

This description of a newly opened flower was made from a rose grown outdoors in the month of September, at Hemet, California:

*Color.*—Outer petal: Outside surface—near Rose Red, Plate 724/3, page 158 (Wilson); inside surface—near Rose Red, Plate 724/1, page 158 (Wilson). Intermediate petal: Outside surface—near Rose Red, Plate 724/3, page 158 (Wilson); Inside surface—near Rose Red, Plate 724/1, page 158 (Wilson). Inner petal: outside surface—near Rose Red, Plate 724/3, page 158 (Wilson); inside surface—near Rose Red, Plate 724/2, page 158 (Wilson).

This description was made from a rose that was open for 3 days in the month of September, at Hemet, California:

*Color.*—Outer petal: Outside surface—near Rose Red, Plate 724/3, page 158 (Wilson); inside surface—near Tyrian Purple, Plate 727, page 159 (Wilson). Inner petal: Outside surface—near Solferino Purple, Plate 26/1, page 26 (Wilson); inside surface—near Tyrian Purple, Plate 727/2, page 159 (Wilson).

*General color effect.*—Newly opened flower—near Rose Red, Plate 724/1, page 158 (Wilson). 3-days open—near Rose Red, Plate 724/2, page 158 (Wilson).

*Behavior.*—Drop off cleanly, except petaloids persist; older flowers tend to burn slightly in extremely hot and dry weather.

*Flower longevity.*—On bush in garden—3 or 4 days in September. Cut roses grown outdoors and kept at living-room temperatures—3 or 4 days in September.

REPRODUCTIVE ORGANS

Stamens: Average number; arranged regularly about pistils; a few mixed with petaloids.

Filaments: Medium length; most with anthers.

Anthers: Small; all open approximately at once. Color: Upper side—near Apricot, Plate 609/1, page 70 (Wilson); under side—near Apricot, Plate 609/2, page 70 (Wilson).

Pollen: Somewhat sparse. Color—near Ochraceous Orange, Plate XV (Ridgway).

Pistils: Average number; approximately 23 in number.

Styles: Moderately even; average length; average caliper; somewhat bunched.

Stigma: Color—near Empire Yellow, Plate 603/1, page 66 (Wilson).

Ovaries: Usualy all enclosed in calyx.

Hips: Average length; globular. Color—near Citron Green, Plate 763/1, page 100 (Wilson), shading to near Orange, Plate 12/1, page 12 (Wilson).

Sepals: Falling soon; medium length; spear-shaped; recurved. Color: Inside—near Light Fluorite Green, Plate XXXII (Ridgway); outside—near Light Bice Green, Plate XVII (Ridgway), shading to near Corinthian Purple, Plate XXXVIII (Ridgway).

Seeds: Very few; from 1 to 5 in number.

PLANT

Foliage:

*Leaves.*—Compound of usually 3 to 7 leaflets; normal quantity; medium size; from moderately heavy to somewhat leathery and semi-glossy.

*Leaflets.*—Elliptic, with apex acute. Base—round. Margin—serrate.

*Color.*—Mature: Upper surface—near Elm Green, Plate XVII (Ridgway); under surface—near Bice Green, Plate XVII (Ridgway). Young: Upper surface—near Spinach Green, Plate V (Ridgway); under surface—near Light Bice Green, Plate XVII (Ridgway), shading to near Corinthian Purple, Plate XXXVIII (Ridgway).

*Rachis (the supporting stem of the compound leaf).*—Average size. Upper side—grooved, with some stipitate glands on edges. Under side—with few prickles and few stipitate glands.

*Stipules.*—Medium length; medium width; with medium length points turning out at an angle of about 45°; recurved toward the stem.

*Disease resistance.*—Better than average resistance to mildew and blackspot, as determined by comparison with other varieties of same class grown under comparable cultural conditions at Hemet, California.

Growth:

*Habit.*—Climbing; moderately branched; mature canes attain length of from 8 to 10 feet.

*Growth.*—Vigorous.

*Canes.*—Medium caliper.

*Main stems.*—Color—near Light Bice Green, Plate XVII (Ridgway). Large prickles—several; medium length; hooked slightly downward; with narrow base of medium length. Color—near Argus Brown, Plate III (Ridgway). Small Prickles—none. Hairs—none.

*Branches.*—Color—near Light Bice Green, Plate XVII (Ridgway). Large prickles—several; medium length; hooked slightly downward; with narrow base of medium length. Color—near Argus Brown, Plate III (Ridgway). Small prickles—none. Hairs—none.

*New Shoots.*—Color—near Elm Green, Plate XVII (Ridgway), shading to near Corinthian Purple, Plate XXXVIII (Ridgway). Large prickles—several; medium length; hooked slightly downward; with narrow base of medium length. Color—near Bice Green, Plate XVII (Ridgway), shading to near Corinthian Purple, Plate XXXVIII (Ridgway). Small prickles—none. Hairs—none.

I claim:

A new and distinct variety of rose plant of the climbing hybrid polyantha class, substantially as herein shown and described, characterized particularly as to novelty by being generally similar to its parent variety "Eutin" (unpatented), but being essentially distinguished therefrom by its vigorous and climbing habit of growth, and its habit of producing flowers in smaller clusters and on shorter stems than those of said parent variety.

No references cited.